US007332502B2

(12) United States Patent
Lee et al.

(10) Patent No.: US 7,332,502 B2
(45) Date of Patent: Feb. 19, 2008

(54) PHENANTHROINDOLIZIDINE ALKALOIDS

(75) Inventors: Shiow-Ju Lee, Tainan (TW); Cheng-Wei Yang, Kaohsiung County (TW)

(73) Assignee: National Health Research Institutes, Miaoli County (TW)

( * ) Notice: Subject to any disclaimer, the term of this patent is extended or adjusted under 35 U.S.C. 154(b) by 163 days.

(21) Appl. No.: 11/151,600

(22) Filed: Jun. 13, 2005

(65) Prior Publication Data

US 2006/0014772 A1   Jan. 19, 2006

Related U.S. Application Data

(60) Provisional application No. 60/579,033, filed on Jun. 11, 2004.

(51) Int. Cl.
*A61K 31/473* (2006.01)
*C07D 221/18* (2006.01)

(52) U.S. Cl. ........................................ 514/283; 546/42
(58) Field of Classification Search ................ 514/283; 546/42
See application file for complete search history.

(56) References Cited

FOREIGN PATENT DOCUMENTS

WO   WO 01/23384   4/2001
WO   03/070166 A2   8/2003

OTHER PUBLICATIONS

Lee et al., "Suppression of nitric oxide production in activated RAW264.7 cells by Phenanthroindolizidine alkaloids," Faseb Journal, vol. 18, No. 8, suppl. S., May 14, 2004, p. C218; Annual Meeting of the American Society for Biochemistry and Molecular Biology; 8th Congress of the In., Boston, MA, USA; Jun. 12-16, 2004, abstract No. 82.43.
Gopalakrishnan et al., "Pharmacological investigations of tylophorine, the major alkaloid of *Tylophora indica*," database accession No. 1979:413829.
Lee et al., "Cytotoxic activity and G2/M cell cycle arrest mediated by antofine, a phenanthroindolizidine alkaloid isolated from cynanchum paniculatum," Planta Medica, Thieme, vol. 69, No. 1, Jan. 2003, pp. 21-25.
Rao et al., "Thymidylate synthase activity in leukocytes from patients with chronic muelocytic leukemia and acute lymphocytic leukemia and its inhibition by phenanthroindolizidine alkaloids pergularine and tylophorinidine," Cancer Letters, 128:183-188, 1997.
Ganguly et al., "Inhibition of cellular immune responses by *Tylophora indicia* in experimental models," Phytomedicine, 8:348-355, No. 8, 2001.
Gopalakrishnan et al., "Pharmacological investigation of tylophorine, the major alkaloid of *Tylophora indica*" Indian J. Med Res 69, pp. 513-520, Mar. 1979.
Wu et al., "Phenanthroindolizidine Alkaloids and Their Cytotoxicity from the Leaves of *Ficus septica*", Heterocycles, vol. 57, No. 12, pp. 2401-2408, Received, Aug. 29, 2002.
Gopalakrishnan, et al., "Effect of Tylophorine, a majoralkaloid of *Tylophora indica*, on immunopathological and inflammatory reactions", Indian J. Med. Res. 71:940-948, 1980.

*Primary Examiner*—Charanjit S. Aulakh
(74) *Attorney, Agent, or Firm*—Occhiuti Rohlicek & Tsao LLP

(57) ABSTRACT

A group of novel phenanthroindolizidine alkaloid compounds as shown and their use in treating cancer. Also disclosed are methods of using phenanthroindolizidine alkoid compounds in suppressing NO and TNF-α production, inhibiting MEKK1 activity and cyclooxygenase II expression, and treating NO-related disorders.

10 Claims, No Drawings

PHENANTHROINDOLIZIDINE ALKALOIDS

RELATED APPLICATIONS

This application claims priority to U.S. Provisional Application No. 60/579,033, filed on Jun. 11, 2004, the contents of which are incorporated herein by reference.

BACKGROUND

Nitric oxide (NO) is an important pleiotropic molecule mediating a wide range of physiological and pathophysiological processes. For example, it enhances activity of cyclooxygenase II (COX-II), which is responsible for the synthesis of the prostagladins that mediate inflammation, pain, and fever (Liu, Q. et al., Cancinogenesis, 2003, Vol. 24, No. 4, 637-642.). As another example, it also increases the expression of signal kinase MEKK1, which plays a key role in the NF-κB activation pathway (Chou F. P. et al., Toxicology and Applied Pharmacology, 2002, Vol. 181, No. 3: 203-206). Overproduction of NO has been implicated in various pathological processes, including septic shock, tissue damage following inflammation, cancer, and rheumatoid arthritis.

NO is produced from L-arginine and molecular oxygen by three distinct isoforms of nitric oxide synthase (NOS), i.e., neural NOS (nNOS), endothelial NOS (eNOS), and inducible NOS (iNOS). Among the three isoforms, iNOS can be induced by endotoxins, cytokines (e.g., TNF-α), or transcriptional factors (e.g., NF-κB and AP1). Inhibiting expression or activity of iNOS is a major target for preventing and eliminating NO overproduction.

SUMMARY

This invention is based on the discovery that certain phenanthroindolizidine alkaloid compounds suppress NO production, inhibit MEKK1 activity, and exert anti-cancer effect.

One aspect of the present invention relates to the compounds of Formula I:

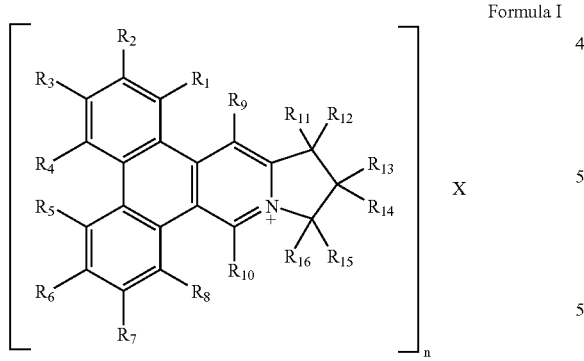

Formula I wherein each of $R_1$, $R_5$, $R_6$, $R_7$, $R_8$, $R_9$, $R_{10}$, $R_{11}$, $R_{12}$, $R_{13}$, $R_{14}$, $R_{15}$, and $R_{16}$, independently, is H, halogen, R, OH, OR, $NH_2$, NHR, or NRR'; and each of $R_2$, $R_3$, and $R_4$, independently, is halogen, R, OH, OR, $NH_2$, NHR, or NRR'; each of R and R', independently, being alkyl, aryl, cyclyl, heteroaryl, or heterocyclyl; X is an anion; and n is the absolute value of the charge of X.

Referring to Formula I, one subset of the compounds feature that each of $R_9$, $R_{10}$, $R_{11}$, $R_{12}$, $R_{13}$, $R_{14}$, $R_{15}$, and $R_{16}$ is H. Another subset of the compounds feature that each of $R_2$, $R_3$, $R_4$, $R_6$, and $R_7$ is $OCH_3$.

An example of the above-described compounds is shown as Compound 1 below.

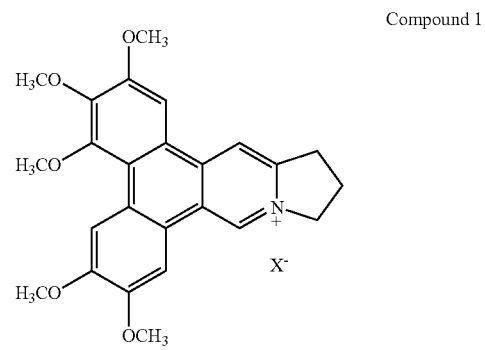

Compound 1

($X^-$ is $Cl^-$, $Br^-$, $I^-$, $OH^-$, $CH_3CO_2^-$, or $CF_3CO_2^-$)

The above-described compounds possess anti-cancer activity. Thus, another aspect of this invention relates to a method of treating cancer by administering to a subject in need thereof an effective amount of one of the compounds. The term "cancer" used herein includes all types of cancerous growths or oncogenic processes, metastatic tissues or malignantly transformed cells, tissues, or organs, irrespective of histopathologic type, or stage of invasiveness. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, and cancer of unknown primary site.

Another aspect of this invention relates to a method for lowering nitric oxide production (via inhibiting expression or activity of iNOS), lowering TNF-α production, lowering COX-II expression, or inhibiting MEKK1 activity. The method includes administering to a subject in need thereof an effective amount of a compound of Formula II:

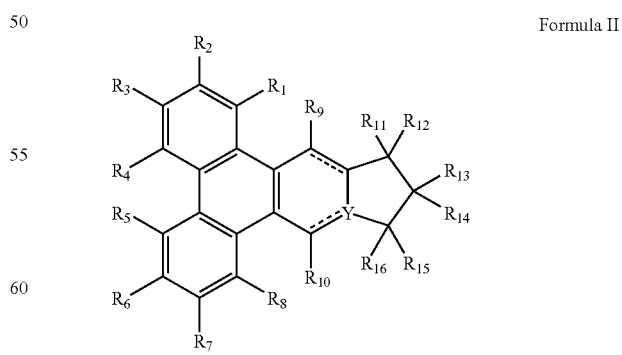

Formula II wherein each of ==== and ====, independently, is a single bond or a double bond; Y is N or $N^+ \rightarrow O^-$, when ==== is a single bond; or Y is $N^+$ and a counterion coexists in the compound, when ==== is a double bond; and each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$, independently, is H, halogen, R, OH, OR, $NH_2$, NHR, or NRR'; each of R and R', independently, being alkyl, aryl, cyclyl, heteroaryl, or heterocyclyl.

Referring to Formula II, one subset of the compounds feature that each of $R_2$, $R_3$, $R_6$, and $R_7$ is $OCH_3$ and each of $R_1$, $R_4$, $R_5$, and $R_8$ is H. Another subset of the compounds feature that each of $R_1$, $R_5$, and $R_8$ is H. $R_4$ is $OCH_3$, and each of $R_9$, $R_{10}$, $R_{11}$, $R_{12}$, $R_{13}$, $R_{14}$, $R_{15}$, and $R_{16}$ is H.

Four exemplary compounds of Formula II are shown below.

Compound 1

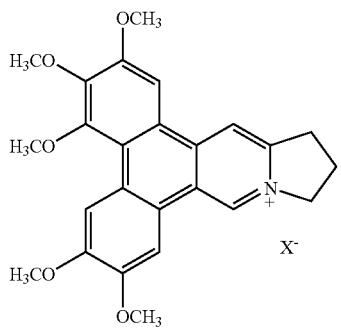

(X⁻ is Cl⁻, Br⁻, I⁻, OH⁻, $CH_3CO_2^-$, or $CF_3CO_2^-$)

Compound 2

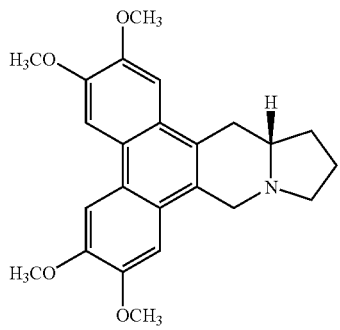

Compound 3

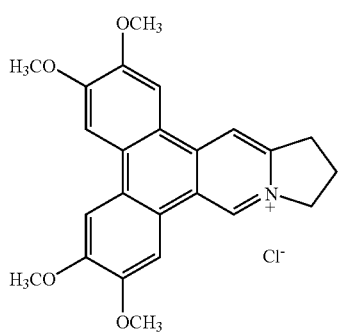

Compound 4

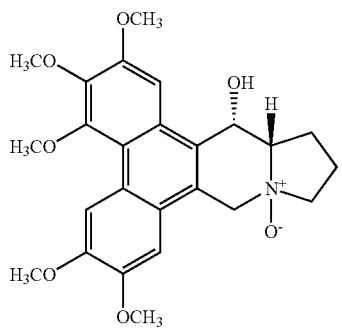

As the compounds of Formula II suppress nitric oxide production, they can be used to treat nitric oxide-related disorders. The nitric oxide-related disorder refers to a disorder associated to overproduction of nitric oxide. Thus, another aspect of this invention relates to a method for treating a nitric oxide-related disorder. The method includes administering to a subject in need thereof an effective amount of a compound of Formula III:

Formula III

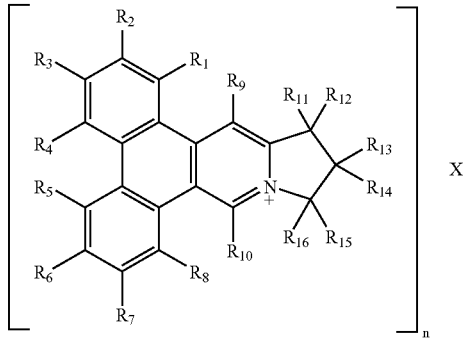

wherein each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$, independently, is H, halogen, R, OH, OR, $NH_2$, NHR, or NRR'; each of R and R', independently, being alkyl, aryl, cyclyl, heteroaryl, or heterocyclyl; X is an anion; and n is the absolute value of the charge of X.

Alternatively, the compound used in the just-described method is one having Formula III:

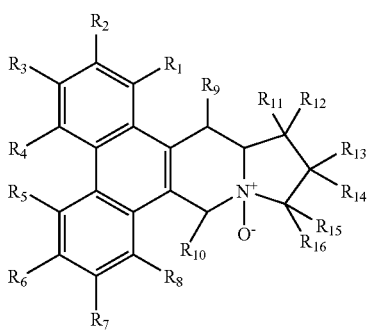

Formula III wherein each of $R_1$, $R_5$, $R_6$, $R_7$, $R_8$, $R_9$, $R_{10}$, $R_1$, $R_{12}$, $R_{13}$, $R_{14}$, $R_{15}$, and $R_{16}$, independently, is H, halogen, R, OH, OR, $NH_2$, NHR, or NRR'; $R_2$, $R_3$, and $R_4$, independently, is halogen, R, OH, OR, $NH_2$, NHR, or NRR'; each of R and R', independently, being alkyl, aryl, cyclyl, heteroaryl, or heterocyclyl.

Referring to Formula III, one subset of the compounds feature that each of $R_9$, $R_{10}$, $R_{11}$, $R_{12}$, $R_{13}$, $R_{14}$, $R_{15}$, and $R_{16}$ is H. Another subset of the compounds feature that each of $R_2$, $R_3$, $R_6$, and $R_7$ is $OCH_3$.

Referring to Formula IV, one subset of the compounds feature that $R_9$ is OH. Another subset of the compounds feature that each of $R_{10}$, $R_{11}$, $R_{12}$, $R_{13}$, $R_{14}$, $R_{15}$, and $R_{16}$ is H.

The term "alkyl" refers to a straight or branched hydrocarbon, containing 1-10 carbon atoms. Examples of alkyl groups include, but are not limited to, methyl, ethyl, n-propyl, i-propyl, n-butyl, i-butyl, and t-butyl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cyclyl" refers to a saturated and partially unsaturated cyclic hydrocarbon group having 3 to 12 carbons, preferably 3 to 8 carbons, and more preferably 3 to 6 carbons, wherein the cyclyl group may be optionally substituted. Examples of cyclyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3,1-6, or 1-9 heteroatoms of N, O, or S if monocyclic, bicyclic, or tricyclic, respectively), wherein each ring may have 1 to 4 substituents. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3,1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

Alkyl, aryl, cyclyl, heteroaryl, and heterocyclyl mentioned herein include both substituted and unsubstituted moieties. Examples of a substituent include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl are optionally further substituted with alkyl, aryl, heteroaryl, halogen, hydroxyl, amino, mercapto, cyano, or nitro.

The term "anion" refers to a negatively charged ion. Examples of an anion include, but are not limited to, $Cl^-$, $Br^-$, $I^-$, $SO_4^{2-}$, $PO_4^{3-}$, $ClO_4^-$, $CH_3CO_2^-$, and $CF_3CO_2^-$.

Also within the scope of this invention is a composition containing one or more of the compounds of Formula I and a pharmaceutically acceptable carrier for use in treating cancer, as well as the use of such a composition for the manufacture of a medicament for treating cancer. In addition, this invention includes a composition containing one or more of the compounds of Formula III or Formula IV and a pharmaceutically acceptable carrier for use in treating a nitric oxide related disorder, as well as the use of such a composition for the manufacture of a medicament for treating a nitric oxide related disorder.

The details of many embodiments of the invention are set forth in the description below. Other features, objects, and advantages of the invention will be apparent from the description and the claims.

DETAILED DESCRIPTION

Some of the above-described phenanthroindolizidine alkaloid compounds can be isolated from plant parts. For example, Compound 2, 3, and 4 can be isolated from leaves of *Ficus septica* (Wu et al. Heterocycles, 2002, 2401). Other compounds can be prepared via simple transformation from one or more of naturally-occurring compounds. For example, Compound 1 can be prepared from Compound 4 via dehydroxylation and dehydration. Scheme 1 shown below depicts the reaction equation of making Compound 1.

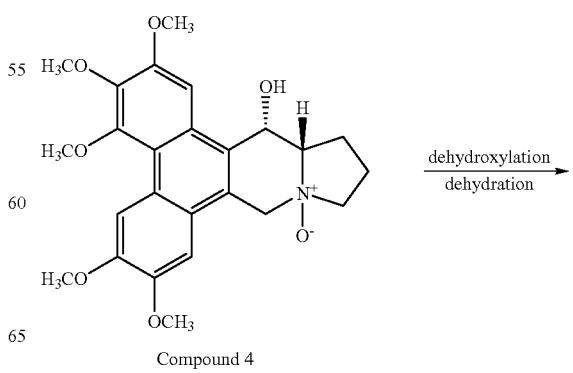

Scheme 1

Compound 4

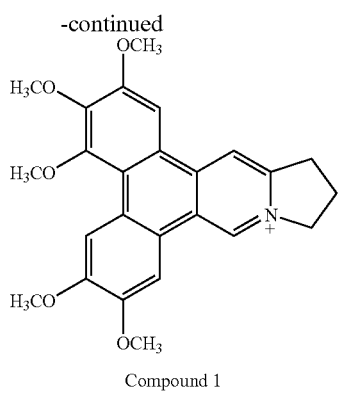

Compound 1

(X⁻ is Cl⁻, Br⁻, I⁻, OH⁻, CH₃CO₂⁻, or CF₃CO₂⁻)

The chemicals used in the above-mentioned isolation and synthesis may include, for example, solvents, reagents, catalysts, and protecting group and deprotecting group reagents. The synthetic method described above may also additionally include steps, either before or after the steps described specifically herein, to add or remove suitable protecting groups in order to ultimately allow synthesis of the desired phenanthroindolizidine alkaloid compounds. Synthetic chemistry transformations and protecting group methodologies (protection and deprotection) useful in synthesizing applicable phenanthroindolizidine alkaloid compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The phenanthroindolizidine alkaloids mentioned above may contain one or more asymmetric centers. Thus, they occur as racemates and racemic mixtures, single enantiomers, individual diastereomers, diastereomeric mixtures, or cis- or trans-isomeric forms. All such isomeric forms are contemplated.

This invention features a method of inhibiting iNOS promoter activity, suppressing nitric oxide production or inhibiting TNF-α, suppressing COX-II expression, inhibiting MEKK1 activity by administering to a subject in need thereof an effective amount of a phenanthroindolizidine alkaloid. The term "an effective amount" refers to the amount of the compound that is required to confer one of the above-described effects on the subject. The effective amount varies, as recognized by those skilled in the art, depending on the types of the effects, route of administration, excipient usage, and the possibility of co-usage with other treatment.

The phenanthroindolizidine alkaloid compounds of Formula I possess anti-cancer activity and the phenanthroindolizidine alkaloid compounds of Formula III or IV inhibit NO production. Thus, this invention covers a method of treating cancer or a nitric oxide-related disorder by administering a phenanthroindolizidine alkaloid compound. Also within the scope of this invention is a pharmaceutical composition containing an effective amount of the phenanthroindolizidine alkaloid compound and a pharmaceutical acceptable carrier. The term "treating" refers to administering the compound to a subject who has a disorder, (i.e., cancer or a nitric oxide-related disorder), or has a symptom of the disorder, or has a predisposition toward the disorder, with the purpose to cure, heal, alleviate, relieve, alter, remedy, ameliorate, improve, or affect the disorder, the symptoms of the disorder, or the predisposition toward the disorder.

A nitric oxide-related disorder is a disorder or condition associated to overproduction of NO, such as an inflammatory disease. An inflammatory disease is characterized by a local or systemic, acute or chronic inflammation. Examples of an inflammatory diseases include systemic lupus erythematosus, encephalitis, meningitis, arthritis, atherosclerosis, hepatitis, sepsis, sarcoidosis, psoriasis, Type I diabetes conjunctivitis, asthma, arteriosclerosis, chronic obstructive pulmonary disease, sinusitis, dermatitis, inflammatory bowel disease, ulcerative colitis, Crohn's disease, Behcet's syndrome, and graft rejection.

To practice the method of the present invention, a composition having one or more of the above-described phenanthroindolizidine alkaloid compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active phenanthroindolizidine alkaloid compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active phenanthroindolizidine alkaloid compound. Examples of other carriers include colloidal silicon oxide, magnesium stearate, cellulose, sodium lauryl sulfate, and D&C Yellow #10.

The above-described effects of a phenanthroindolizidine alkaloid compound can be tested by an in vitro or in vivo assay. For example, compounds of Formula I can be preliminarily screened by in vitro assays in which the compounds are tested for their efficacy in inhibiting cancer cell growth. Compounds that demonstrate high efficacy in the preliminary screening can be further evaluated by in vivo methods well known in the art to evaluate their activity in treating cancer.

Similarly, compounds of Formula III or IV can be screened by an in vitro assay for their activity of suppressing nitric oxide production. Compounds that demonstrate high activity can be further evaluated by in vivo assays to evaluate their activity of treating a nitric oxide-related disorder.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compounds 1-4

Compounds 2, 3, and 4 were isolated from the leaves of *Ficus septica* according to the method described in Wu et al. Heterocycles, 2002, 2401. Compound 4 was dehydroxylated and dehydrated to afford Compound 1.

EXAMPLE 2

Biological Assays

Inhibition of iNOS Promoter Activity

RAW 264.7 cells (or A549 cells) were seeded in 24-well plates ($9 \times 10^4$ cells/well) and grown overnight in sodium pyruvate-free DMEM with 4 mM glutamine containing 1% non-essential amino acids (Biological Industries, Israel) with antibiotics and 10% heat-inactivated fetal bovine serum or 10% fetal calf serum (Biological Industries, Israel). The cells were then co-transfected with murine or human iNOS or murine COX-II promoter-luciferase reporter plasmids (100 ng/well) and pCMV-P-gal (100 ng/well) using FuGene6 (Roche, Germany) following the protocol provided by the manufacturer. Murine iNOS promoter luciferase plasmids, human iNOS promoter-luciferase reporter plasmids (pGL3-8296), and murine COX-II promoter-luciferase reporter plasmids were generously provided by Drs. Charles J. Lowenstein (John Hopkines University), Joel Moss (National Institute of Health), and Yu-Chih Liang (Taipei Medical University), respectively.

The cells were incubated for 24 h and the culture medium was replaced with one containing 5 µg/ml lipopolysaccharide (LPS), 20 ng/ml IFNγ, and each of Compounds 1-4 (final concentration: 10 µM). After 18-20 h, the medium was removed and 150 µl of Glo lysis buffer was added to each well. The resultant lysates were subjected to the luciferase and β-galactosidase assays. Transfection efficiency was normalized by β-galactosidase activity.

The luciferase and β-galactosidase assays were performed using a STEADY-GLO luciferase assay system (Promega) and Galacto-Star assay system (Tropix) according to the manufacturer's instructions. Luminescence was measured in a TOPCOUNT.NXT™ Microplate Scintillation and Luminescence Counter (Packard Inc.). The results were normalized to β-galactosidase activity derived from co-transfected LacZ gene under the control of a constitutive promoter.

The results show that Compounds 2 and 4 effectively inhibited iNOS promoter activity.

Inhibition of AP1 and NF-κB Activity:

RAW 264.7 cells (or A549 cells) were seeded in 24-well plates ($10^6$ cells/well) 4-6 h before they were transfected with pNF-κB-Luc (Stratagene Corp., CA) (100 ng/well) and pCMV-β-gal (100 ng/well), or pAPI-Luc (Stratagene Corp., CA) (200 ng/well) alone. The transfected cells were incubated for 24 h and then washed with the culture medium twice. After 18 h of incubation, the cells were treated with LPS (10 µg/ml)/IFNγ (20 ng/ml) and Compound 2 (final concentration: 0.3, 1, 3, or 10 µM) for 5 h. The cells were subjected to the luciferase and P-galactosidase assays. Of note, in the assay involving pNF-κB-Luc, the culture medium was free of serum; and in the assay involving pAP1-Luc, the culture medium did not include non-essential amino acids. The results show that Compound 2 at the concentration higher than 1 µM inhibited AP1 activity, but not NF-κB activity.

In a similar manner, RAW264.7 cells were transfected with pNF-κB-Luc plasmids (100 ng/well) or pAP1-Luc (100 ng/well) as well as pFC-MEKK (Stratagene Corp., CA) (50 ng/well) and/or pCMV-β-gal plasmids (100 ng/well) and the transfected cells were subjected to the luciferase and β-galactosidase assays. The results show that Compound 2 at the concentration of 3 µM or higher inhibited activity of AP1 or pNF-κB in the cells which was treated with LPS/IFNγ and had over-expression of MEKK1. The results suggest that Compound 2 inhibited MEKK1 activity or expression. The extent of the inhibition was comparable to that observed in the cells which had over-expression of MEKK1, but was not treated with LPS/IFNγ.

In addition, it was observed that Compound 2 enhanced phosphorylation of Akt (a serine/threonine kinase) and ATF-2 (a transcriptional factor), and inhibited expression of c-Jun (a component of the transcription factor AP1) in LPS/IFNγ-treated RAW264.7 cells. Also, Compound 2 and another P13K/Akt inhibitor, e.g., LY294002 (Vlahos, C. J. et al. J. Immunol. 1995, 154: 2413), significantly inhibited NF-κB activity.

Inhibition of Carcinoma Cell Growth:

Two cancer cell lines, HONE-1 (nasopharyngeal carcinoma) and NUGC-3 (gastric cancer), were maintained in DMEM medium containing 10% fetal bovine serum, seeded in 96-well plates (4500 and 6000 cells/well, respectively), and incubated under $CO_2$ at 37° C. for 24 h. The cells were treated with at least five different concentrations of test compounds in a $CO_2$ incubator for 72 h. The number of viable cells was estimated using the tetrazolium dye reduction assay (MTS assay) according to the protocol provided by the manufacturer (Promega, Madison, Wis., USA). The absorbance was measured at 490 nm on a Wallac 1420

VICTOR2 Multilabel counter (Perkin-Elmer, Boston, Mass.). The results of these assays were used to obtain the dose-response curves from which $IC_{50}$ (nM) values were determined (an $IC_{50}$ value represents the concentration (nM) of the test compound at which it produces a 50% cell growth inhibition after 3 days of incubation). The results show that Compound 1, 2, and 4 inhibited proliferation of HONE-1 and NUGC-3 cells.

Inhibition of Nitric Oxide and TNF α Production and iNOS and COX-II Expression:

RAW 264.7 cells were seeded (70,000 cells/well) and cultured in 96-well culture plate. After 24 h incubation, the medium was replaced with one containing LPS (5 ug/ml)/ IFNγ (20 ng/ml) and each of Compounds 1-4 (final concentration: 3, 5, or 6 μM) was added at different concentrations. After 18-24 h, the supernatants were subjected to the measurement of nitric oxide production using the Nitrate/Nitrite assay kit (Cayman Chemical). Nitric oxide levels were measured as the accumulation of nitrite and nitrate in the incubation medium. Nitrate was reduced to nitrite with nitrate reductase and determined spectrophotometrically with the Griess reagent at $OD_{405}$. The attached cells were subjected to cytotoxicity measurement using the MTS assay. The results show that Compounds 1-4 inhibited production of NO.

An ELISA kit (R & D Systems Inc., USA) was used to measure TNF α protein in cell culture supernatants using according to the manufacturer's instructions. The results show that Compound 2 inhibited production of TNF α.

Levels of iNOS, COX-II, and β-actin (control) were measured by immunoblotting with anti-iNOS antibody (Biomol), anti-COX-II antibody (Upstate), and anti-β-actin antibody (Chemicon), respectively. The cell lysates were subjected to SDS-PAGE and the separated proteins were electrophoretically transferred to nitrocellulose membranes. The membranes were incubated, respectively, with blocking solution for 1 h, primary antibody for 2 h, and secondary antibody for 1 h. Antigen-antibody complexes were detected using ECL detection reagents (Perkin Elmer, Western Blot Chemiluminescence Reagent Plus) according to the manufacturer's instructions. The results show that Compound 2 lowered both iNOS and COX-II levels.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to above-described phenanthroindolizidine alkaloid compounds also can be made, screened for the above-described activities and used to practice this invention. Thus, other embodiments are also within the claims.

What is claimed is:

1. A compound of the following formula:

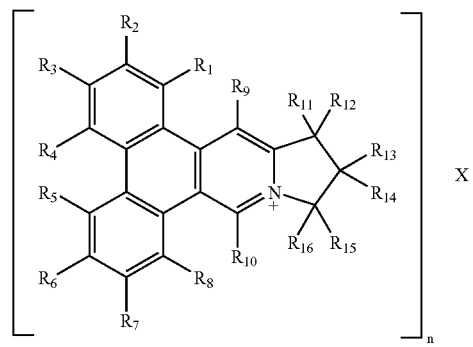

wherein
each of $R_1$, $R_5$, $R_6$, $R_7$, $R_8$, $R_9$, $R_{10}$, $R_{11}$, $R_{12}$, $R_{13}$, $R_{14}$, $R_{15}$, and $R_{16}$, independently, is H, halogen, R, OH, OR, $NH_2$, NHR, or NRR'; and each of $R_2$, $R_3$, and $R_4$, independently, is halogen, R, OH, OR, $NH_2$, NHR, or NRR'; each of R and R', independently, being alkyl, aryl, cyclyl, heteroaryl, or heterocyclyl;
X is an anion; and
n equals the absolute value of the charge of X so that the overall charge of the compound is 0.

2. The compound of claim 1, wherein each of $R_9$, $R_{10}$, $R_{11}$, $R_{12}$, $R_{13}$, $R_{14}$, $R_{15}$, and $R_{16}$ is H.

3. The compound of claim 2, wherein each of $R_6$ and $R_7$ $OCH_3$.

4. The compound of claim 3, wherein each of $R_1$, $R_5$, and $R_8$ is H.

5. The compound of claim 4, wherein each of $R_2$, $R_3$, and $R_4$ is $OCH_3$.

6. The compound of claim 1, wherein each of $R_2$, $R_3$, $R_4$, $R_6$, and $R_7$ is $OCH_3$.

7. The compound of claim 6, wherein each of $R_1$, $R_4$, $R_5$, and $R_8$ is H.

8. A method for suppressing nitric oxide production, comprising administering to a subject in need thereof an effective amount of a compound of the following formula:

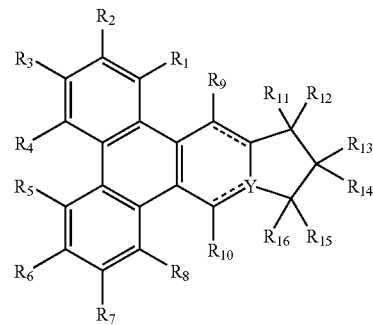

wherein each of ==== and ---- is a double bond, Y is $N^+$, and counterion coexists in the compound; $R_2$, $R_3$, $R_6$, and $R_7$ $OCH_3$; $R_1$, $R_4$, $R_5$, and $R_8$ is H; and each of $R_9$, $R_{10}$, $R_{11}$, $R_{12}$, $R_{13}$, $R_{14}$, $R_{15}$ and $R_{16}$, independently, is H, halogen, R, OH, OR, $NH_2$, NHR, or NRR'; each of R and R', independently, being alkyl, aryl, cyclyl, heteroaryl, or heterocyclyl.

9. A method for suppressing nitric oxide production, comprising administering to a subject in need thereof an effective amount of a compound of the following formula:

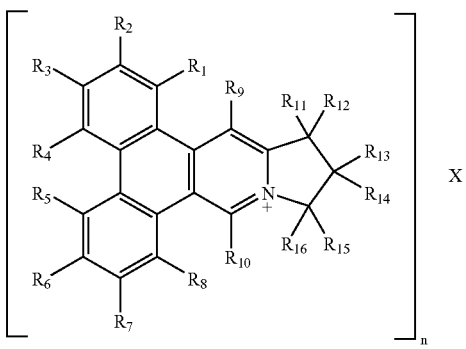

wherin each of $R_1$, $R_5$, $R_6$, $R_7$, $R_8$, $R_9$, $R_{10}$, $R_{11}$, $R_{12}$, $R_{13}$, $R_{14}$, $R_{15}$, and $R_{16}$, independently, is H, halogen, R, OH, OR, $NH_2$, NHR, or NRR'; and each of $R_2$, $R_3$, and $R_4$, independently, is halogen, R, OH, OR, $NH_2$, NHR, or NRR'; each of R and R', independently, being alkyl, aryl, cyclyl, heteroaryl, or heterocyclyl;

X is an anion; and n equals the absolute value of the overall charge of the compound is 0.

10. The method of claim 9, wherein each of $R_1$, $R_5$, and $R_8$ is H, and $R_4$ is $OCH_3$.

* * * * *